United States Patent [19]
Liebig et al.

[11] Patent Number: 5,672,877
[45] Date of Patent: Sep. 30, 1997

[54] COREGISTRATION OF MULTI-MODALITY DATA IN A MEDICAL IMAGING SYSTEM

[75] Inventors: John R. Liebig, San Jose; Steven M. Jones, Pleasanton; Xiaohan Wang, Alameda, all of Calif.

[73] Assignee: ADAC Laboratories, Milpitas, Calif.

[21] Appl. No.: 623,908

[22] Filed: Mar. 27, 1996

[51] Int. Cl.[6] .................................................. G01T 1/166
[52] U.S. Cl. ................................................... 250/363.04
[58] Field of Search ................. 378/63, 162; 250/363.04

[56] References Cited

U.S. PATENT DOCUMENTS

| | | | |
|---|---|---|---|
| 4,884,566 | 12/1989 | Mountz et al. | 378/205 |
| 5,210,421 | 5/1993 | Gulberg et al. | 250/363.04 |
| 5,299,253 | 3/1994 | Wessels | 378/20 |
| 5,391,877 | 2/1995 | Marks | 250/363.04 |
| 5,598,003 | 1/1997 | Jones et al. | 250/363.04 |

*Primary Examiner*—Carolyn E. Fields
*Attorney, Agent, or Firm*—Blakely, Sokoloff Taylor & Zafman LLP

[57] ABSTRACT

A method of coregistering medical image data of different modalities is provided. In the method, an emission scan of an object is performed using a nuclear medicine imaging system to acquire single-photon emission computed tomography (SPECT) image data. A transmission scan of the object is performed simultaneously with the emission scan using the same nuclear medicine imaging system in order to acquire nuclear medicine transmission image data. The emission scan is performed using a roving zoom window, while the transmission scan is performed using the full field of view of the detectors. By knowing the position of the zoom windows for each detection angle, the nuclear medicine transmission image data can be coregistered with the SPECT emission image data as a result of the simultaneous scans. Image data of a modality other than SPECT, such as x-ray computed tomography (x-ray CT) data, magnetic resonance imaging (MRI) data, or positron emission tomography (PET) data, is also provided, which it is desired to have coregistered with the SPECT emission data. The nuclear medicine transmission image data is therefore coregistered with the image data of the different modality. As a result, the image data of the different modality becomes coregistered with the SPECT image data.

22 Claims, 9 Drawing Sheets

COREGISTRATION OF MULTI-MODALITY DATA IN A MEDICAL IMAGING SYSTEM

FIELD OF THE INVENTION

The present invention pertains to the field of medical imaging. More particularly, the present invention relates to a method and apparatus for coregistering medical images from different imaging modalities.

BACKGROUND OF THE INVENTION

In the practice of medicine, various techniques are available for obtaining diagnostic images of the human body. Examples of such techniques are computed tomography (CT), ultrasound imaging, and fluoroscopy. CT encompasses a broad range of imaging methods, including single-photon emission computed tomography (SPECT), positron emission tomography (PET), and magnetic resonance imaging (MRI). SPECT and PET are also sometimes categorized under the general term, "nuclear medicine". Each of these imaging techniques, or "modalities", employs different methods of acquiring data and yields images having unique characteristics.

Because of the differences between the various imaging modalities, a given modality may be particularly useful for obtaining a specific type of diagnostic information but inadequate for obtaining other types of diagnostic information. SPECT, for example, is often used to obtain images of organs which contain both structural (anatomical) and functional information about that organ. However, SPECT and other nuclear medicine techniques tend to be organ-specific; that is, images from these modalities tend to show a particular organ of interest but yield little or no information about the anatomical structures surrounding that organ. Generally, in nuclear medicine techniques a radiopharmaceutical is first injected into a patient. The radiopharmaceutical concentrates in a particular organ, such as the heart or the brain, and causes radiation to be emitted from that organ. The radiation is then detected by the imaging equipment and used to generate images. The resulting images provide substantial information about the organ of interest but generally do not show skeletal structures or other nearby organs (such as the lungs, when imaging the heart). However, a physician may require such additional information to make an accurate diagnosis or to administer proper treatment.

In nuclear medicine, if the physician requires images of anatomical structures other than the primary organ of interest, the physician generally must resort to other modalities, such as x-ray CT or MRI. When images from more than one modality are available, the physician may wish to combine information in the separate images into one image. For example, the physician may wish to view the images as superimposed upon each other, so that a location in the body represented in one image can be more easily and more accurately related to the other images. The superimposing of different images of the same subject matter is sometimes referred to as "coregistration". In the context of medical imaging, "coregistration" may be defined more specifically as a process of combining two or more images of the same region of the body to form one combined image, such that a given point in the body is represented by only one point in the combined image (i.e., the individual images are precisely lined up). The coregistered images might be displayed on a computer screen, or they might be viewed on some form of hard output, such as paper, x-ray film, or other similar mediums.

Various methods are known in the prior art for coregistering images from different modalities. However, coregistering multi-modality images with both ease and accuracy is a problem associated with these methods. For example, images from different modalities can be coregistered by eye. More specifically, one might manipulate a mouse or trackball of a computer system to move medical images displayed on a computer monitor. However, this method is generally not very accurate, because often there is insufficient common information between images of different modalities to use as reference points.

Another coregistration method involves the use of "markers". Markers are objects that are placed next to a patient during imaging and which are visible in images from two or more different modalities. Markers are commonly used to coregister images obtained using nuclear medicine emission images (i.e., SPECT) with nuclear medicine transmission images. Nuclear medicine transmission imaging is discussed in greater detail in the detailed description which follows. A marker may constitute a small piece of metal, or a container filled with a radionuclide substance. In this method, imaging scans are performed using different modalities, one modality at a time, such that the markers are placed in the same locations relative to the patient's body for each scan. Since the markers appear in each of the resulting images, the images of different modalities can be coregistered. However, precisely fixing the location of the markers relative to the patient's body can be problematic. The patient may move slightly between scans and during scans, and if there is patient movement relative to the markers, it becomes difficult or impossible to accurately coregister the resulting images.

Hence, what is needed is an improved method of coregistering multi-modality medical imaging data, which overcomes the above-mentioned drawbacks. In particular, what is needed is a method which provides a relatively easy and accurate way of coregistering multi-modality medical imaging data.

SUMMARY OF THE INVENTION

A method of coregistering medical image data of different modalities is provided. In the method, an emission scan of an object is performed using a nuclear medicine imaging system. During the emission scan, single-photon emission computed tomography (SPECT) image data is acquired. Simultaneously with the emission scan, a transmission scan of the object is performed using the same nuclear medicine imaging system to acquire nuclear medicine transmission image data. The acquired nuclear medicine transmission image data is coregistered with the SPECT image data. Image data of a modality other than SPECT is provided, which it is desired to have coregistered with the SPECT data. Consequently, the nuclear medicine transmission image data is coregistered with the image data of the other modality, and as a result, the image data of the other modality becomes coregistered with the SPECT image data.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A method and apparatus for coregistering images from different modalities in a medical imaging system are described. In the following description, for purposes of explanation, numerous specific details are set forth in order to provide a thorough understanding of the present invention. It will be evident, however, to one skilled in the art that the present invention may be practiced without these specific details. In other instances, well-known structures and devices are shown in block diagram form in order to avoid unnecessarily obscuring the present invention.

In the following description, unless specifically stated otherwise, discussions relating to functions of the computer system of the present invention utilizing terms such as "processing" or "computing" or "calculating" or "determining" or "displaying" or the like, refer to the action of a computer system, or similar electronic computing device, that is executing a program to manipulate and transform data represented as physical (electronic) quantities within the computer system's registers and memories into other data similarly represented as physical quantities within the computer system memories or registers.

I. Overview

In nuclear medicine imaging (i.e., SPECT and PET), a patient is injected with a radiopharmaceutical that tends to accumulate within a particular organ of interest. A gamma camera is then used to detect emitted gamma rays, or photons, from various angles around the body. Photons reaching the gamma camera's scintillation detectors cause scintillation events, which are detected by photomultiplier tubes and then converted by circuitry into electrical signals representing both position and energy information. These signals are then used to generate image data in a process known as reconstruction. The resulting images may be referred to as "emission images".

Another technique frequently used in nuclear medicine is "transmission imaging". Transmission imaging is commonly used to correct for the effects of photon attenuation in the emission images. Tissue and bone structure surrounding the organ of interest tend to attenuate photons emitted from the radiopharmaceutical distributed within the organ. Since each patient is different (different size, shape, etc.), the tissue and bone structure surrounding the organ of interest are different for each patient. The attenuation of the radiation is non-uniform because the attenuation coefficients of the different tissues and bone are different. Such non-uniform attenuation can substantially reduce image quality. However, transmission imaging allows a gamma camera and a processing computer system to compensate for non-uniform attenuation by generating an "attenuation map" of the body.

Generally, during transmission scanning, radiation from a transmission source having known properties is transmitted through the patient and then detected by a scintillation detector in the gamma camera. By knowing the intensity of the radiation transmitted by the source, and by measuring the intensity of radiation which passes through the object and is detected, a computer within the gamma camera system can determine the extent of non-uniform radiation attenuation over different parts of the body at different angles. From this information, a non-uniform attenuation map of the body can be generated using well-known methods and procedures. The attenuation map is then used during the reconstruction process to correct emission image data for the effects of nonuniform photon attenuation.

In accordance with the present invention, transmission imaging is performed simultaneously with emission imaging using a nuclear medicine (gamma camera) imaging system. The image data resulting from the transmission scan is then used to coregister the emission image data with image data from other modalities, as will be described in detail below.

II. Imaging System

Figure 1:
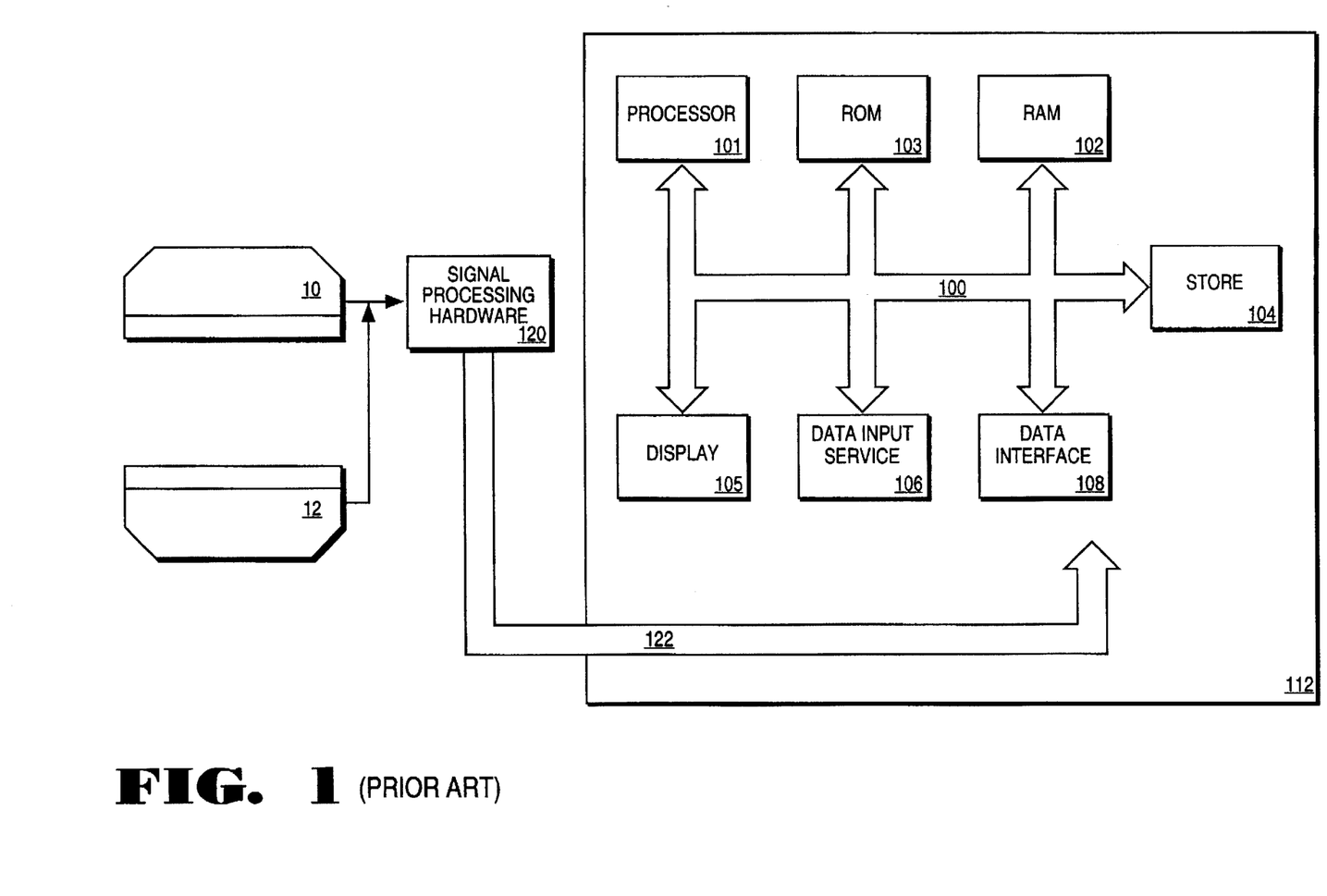
FIG. 1 is a block diagram of a gamma camera medical imaging system.

FIG. 1 illustrates in block diagram form a nuclear medicine imaging system which can be used to implement the present invention. The imaging system of FIG. 1 may be used for either SPECT or PET imaging. The imaging system includes a general purpose computer system 112 used for processing image information supplied from scintillation detectors 10 and 12. The computer system 112 also controls movement of detectors 10 and 12 on a gantry and controls motion controllers for controlling the movement of transmission line sources, which are discussed below.

The computer system 112 includes an address/data bus 100 for communicating information within the system; a central processing unit (CPU) 101 coupled to the bus 100 for executing instructions and processing information; a random access memory (RAM) 102 coupled to the bus 100 for storing information and instructions for the central processor 101; a read only memory (ROM) 103 coupled to the bus 100 for storing static information and instructions for the processor 101; a mass storage device 104 coupled to the bus 100 for storing image information and instructions; a display device 105, such as a cathode ray tube (CRT), coupled to the bus 100 for displaying information to computer user; an alphanumeric input device 106 including alphanumeric and function keys coupled to the bus 100 for communicating information and command selections to the central processor 101; a cursor control device (which may be part of the data input device 106) coupled to the bus for communicating user input information and command selections to the central processor 101; and, a data interface device 108 coupled to the bus 100 for communicating command selections to the processor 101. A "hardcopy" output device, such as a printer, may also be coupled to bus 100.

The display device 105 in FIG. 1 may comprise a cathode ray tube (CRT), a liquid crystal display (LCD), or other device suitable for displaying images and alphanumeric characters to the user. The cursor control device allows the computer user to dynamically signal the two dimensional movement of a visible symbol (pointer) on a display screen of the display device 105. Many implementations of the cursor control device are known in the art including a trackball, finger pad, mouse, joystick or special keys on the alphanumeric input device 106 capable of signaling movement of a given direction or manner of displacement. The mass storage device 104 may be a magnetic or optical disk and disk drive, or other similar device.

The computer system 112 interfaces with scintillation detectors 10 and 12 via signal processing hardware circuits 120 over bus 122. The signal processing hardware 120 comprises amplification circuitry and analog-to-digital conversion circuits for converting channel signals from the detectors to digital data for transmission to the computer system 112. In particular, signal processing hardware 120 converts the outputs of photomultiplier tubes in detectors 10 and 12 into spatial coordinate data and energy data for detected scintillation events.

Transmission and emission data are stored in memory 102 in matrix form. Separate matrices may be used to store the transmission and emission data, respectively. Nonuniform attenuation maps derived from transmission scanning are also stored in memory 102 in matrix form. Each cell, or "bin", of a matrix corresponds to one pixel in an output image. Once image matrices are collected at different rotation angles, tomographic reconstruction is performed to generate multiple slice images or a three-dimensional image of an organ.

Figure 2:
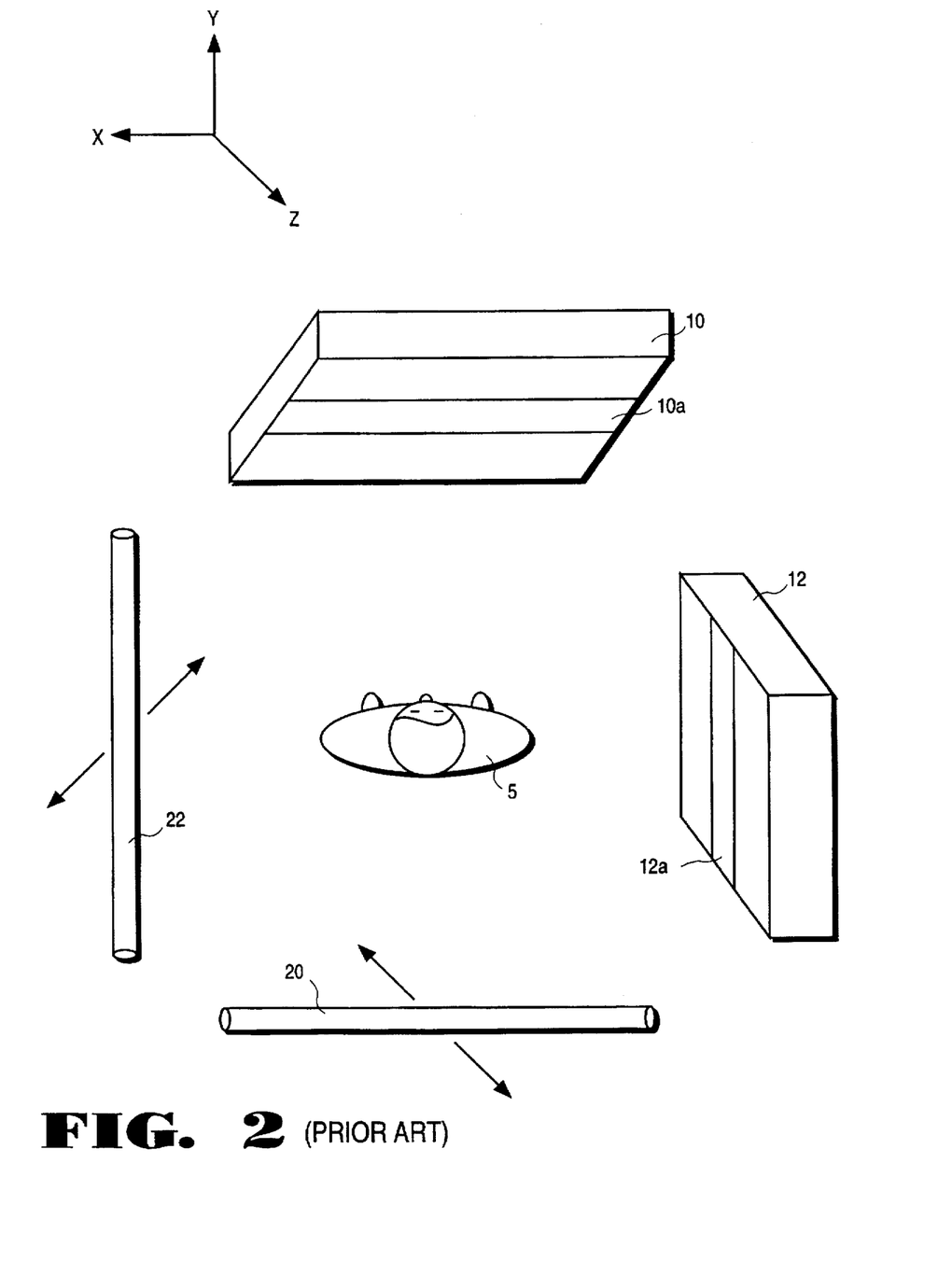
FIG. 2 illustrates detectors and transmission line sources of a gamma camera system configured to perform a transmission scan of a patient.

FIG. 2 shows portions of a gamma camera system configured to perform a transmission scan of a patient 5. When performing the transmission scan, scintillation detectors 10 and 12 are positioned in a 90° relative orientation, as shown in FIG. 2. Transmission line sources 20 and 22 are used to transmit gamma radiation through the patient 5 to detectors 10 and 12, respectively. For various different angles about the Z axis (rotation angles), line source 20 is translated across the field-of-view (FOV) of detector 10, and line source 22 is translated across the FOV of detector 12. Detectors 10 and 12 then measure the amount of radiation from line sources 20 and 22, respectively, that passes completely through the patient 5. Transmission detection region 10a receives collimated radiation as the transmission line source 20 travels along the axis Z. Region 10a scans in synchronization with line source 20. Similarly, transmission region 12a receives collimated radiation as line source 22 travels along axis Z. Region 12a moves in synchronization with assembly 22. Using the configuration of FIG. 2, transmission scanning may be performed simultaneously with emission scanning, provided different radiation energy levels are assigned for the emission and transmission scans.

A. Roving Zoom Windows

In certain SPECT imaging applications, such as cardiac imaging, it is desirable to image an organ with a high resolution image matrix (e.g., having small pixel sizes) because of the small size of the organ. In order to achieve sufficiently small pixel sizes, a small FOV (SFOV) detector is sometimes used. For example, detectors having a physical field of view of 16"×16", 15"×15" and 13"×13" may be used. However, for a transmission scan to yield an accurate attenuation map of the body, the full field of view of a large detector (e.g., 20"×15") is needed to avoid truncation of the body. Consequently, the currently preferred embodiment of the present invention uses a large FOV (LFOV) for the transmission scan but allows a SFOV to be used for the emission scan.

In the preferred embodiment, the SFOV used for the emission scan is implemented using a roving zoom "window" or region, which is described in detail in U.S. Pat. No. 5,304,806, entitled, "Apparatus and Method for Automatic Tracking of a Zoomed Scan Area in a Medical Camera System," issued Apr. 19, 1994, and assigned to the assignee of the present invention. The zoom window detects emission radiation from the organ of interest (e.g., the heart). Because the pixels are smaller within the zoom region than outside the zoom region, the emission image appears larger and therefore "zoomed."

In the preferred embodiment, a zoom window is defined within the FOV of each detector by the detector electronics and/or computer system's data acquisition processes. This window is defined to coincide with the portion of the FOV of each detector which coincides with a particular organ, such as the heart. The detector electronics provide image magnification for emission radiation detected within the zoom windows. As the detectors rotate about the object to a different angle, the zoom windows displace ("rove") relative to the surface of the detectors, so that the heart (or other organ of interest) remains centered and within the FOV of each zoom window. In effect, the zoom windows track the organ for each rotation angle. Since the zoom windows are smaller than the entire FOV of a detector, the image rendering capacity of the gamma camera can be focused on the zoom window, and the resultant image generation quality is increased (e.g., resolution is increased). The details regarding the tracking of the zoom windows in a dual detector system are described in U.S. Pat. No. 5,304,806, as noted above.

B. Data Acquisition

Figure 3:
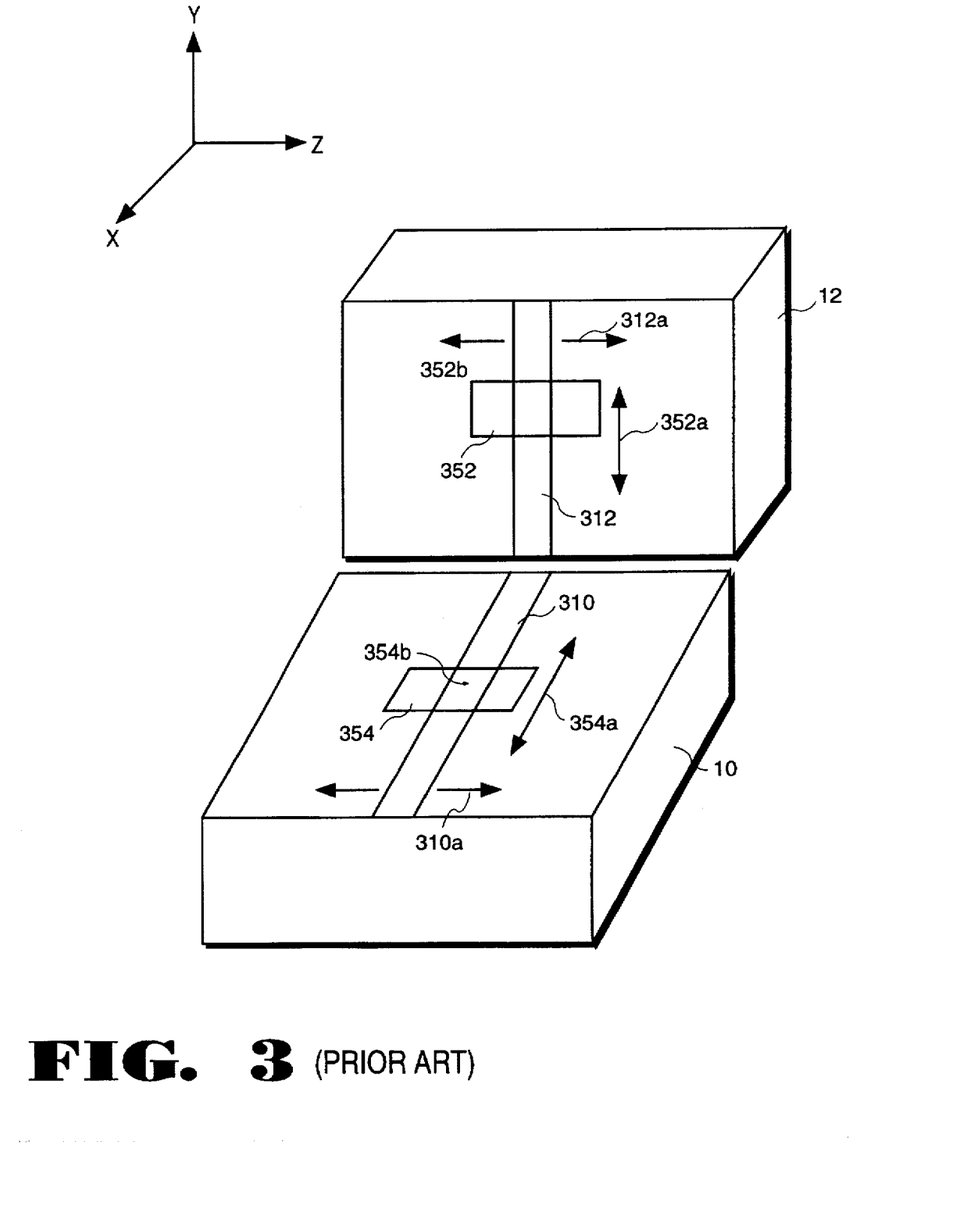
FIG. 3 illustrates tracking zoom windows and scanning transmission detection windows with respect to two detectors.

FIG. 3 illustrates how tracking zoom windows are implemented in conjunction with the transverse dual-detector transmission window and dual line source scanning configuration of the present invention. Zoom windows 352 and 354 are defined on the surface of detectors 12 and 10, respectively, and move up and down as shown by arrows 352a and 354a in order to track an object of interest as detectors 10 and 12 rotate about the z axis. For any given angle, the positions of zoom windows 352 and 354 remain fixed. The detectors 10 and 12 electronically collect emission data (e.g., counts) only within the zoom regions 352 and 354 for each angle of rotation. Although the entire FOV of the detector 10 and 12 may be receiving emission radiation, only emission radiation that is detected within the zoom windows 352 and 354 is stored and used for image reconstruction.

Simultaneous with the collection of emission data within the two roving zoom windows, transmission data is also collected within scanning transmission detection windows 310 and 312. An exemplary implementation uses TI-201 as the emission radiation source and Gd-153 as the transmission radiation source. Although not shown in FIG. 3, two scanning line sources are also present and move in synchronization with the two transmission detection windows, as discussed previously. For each angle of rotation about the z axis, the transmission detection windows 310 and 312 scan across the FOV of the detector according to arrows 312a and 310a in order to collect transmission data. Also, for each angle or rotation, zoom windows 352 and 354 assume a new spatial position (rove) to track the object of interest. However, unlike the scanning transmission detection windows 312 and 310, at any given angle of rotation the zoom windows 352 and 354 remain stationary relative to the detector surface.

The transmission detection windows 310 and 312 of the present invention report only photons within the transmission energy level and reject other detected photons, e.g., emission energy level photons which result from: (1) scattered transmission photons; and (2) nonscattered emission photons. The zoom regions 352 and 354 report emission photons because collimation of the line sources and the detector ensures that no valid transmission photons fall outside the two transmission detection windows 310 and 312.

As shown in FIG. 3, transmission detection windows 310 and 312 will, at times, partially coincide with zoom windows 352 and 354 as they scan across the FOV of their associated detectors. During such times, electronics within the imaging system provide correction, so that emission photons falling within transmission detection regions 310 and 310 are not incorrectly interpreted as transmission photons, and so that transmission photons received within zoom windows 352 and 354 are not incorrectly interpreted as emission photons. The details of how such correction is performed is beyond the scope of this description and is not necessary for understanding the present invention.

III. Coregistration of Nuclear Medicine Emission and Transmission Images

For purposes of tomographic reconstruction, the images taken at each rotation angle assume that there is a fixed center of rotation and that the objects imaged are steady with respect to that center of rotation. However, with respect to a roving zoom region, since the emission acquisition window displaces relative to the detector surface to track an organ, effectively the emission tomogram has a virtual center of rotation; that is, the imaged organ becomes the virtual center of rotation. Further, this virtual center of rotation may not be the same as the actual physical center of rotation defined by the gantry and detector mechanisms. It should be appreciated that, if the imaged organ were located at the physical center of rotation, then the zoom region would not need to rove at all.

In the preferred embodiment, in which emission data is acquired through the roving zoom region, the transmission data (which is acquired simultaneously with the emission data) is spatially shifted to account for the "virtual" center of rotation defined by the imaged organ. Specifically, because the roving zoom region displaces a given distance for a given angle of rotation, the transmission data collected for that angle must also be shifted, or "offset", to account for this displacement. Hence, during reconstruction of the transmission and emission data, like points in the body are reconstructed in the same position on the transmission images as on the emission images. That is, the transmission images (e.g., the attenuation map) will be spatially aligned with the emission images In addition, since the transmission pixels are larger than the emission pixels, as explained above, the pixel size of the transmission dataset matrices must be adjusted to match the zoom region pixel size. The adjustment of pixel size will be described below in detail. Once the transmission dataset has been adjusted to correct for the zoom region displacements and different pixel size, the transmission data will be effectively coregistered with the emission data, since the two datasets were acquired simultaneously using the same detectors.

Figure 4A:
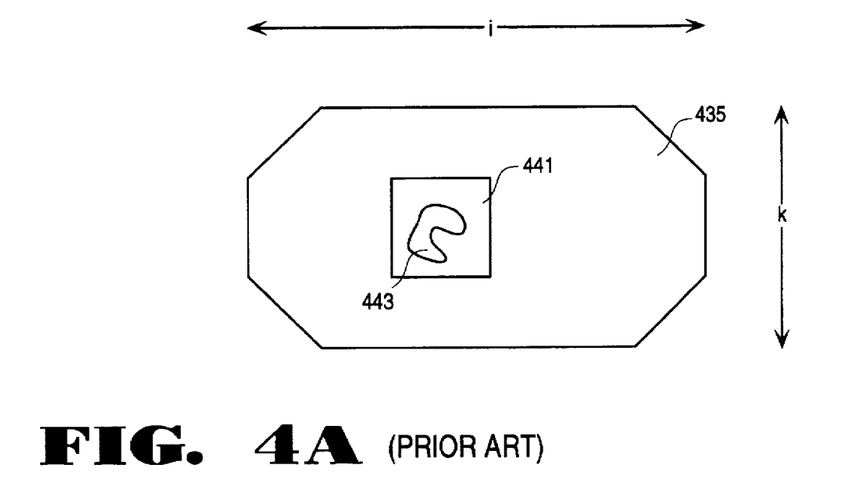
FIGS. 4A and 4B illustrate the use of roving zoom windows for emission scanning
Figure 4B:
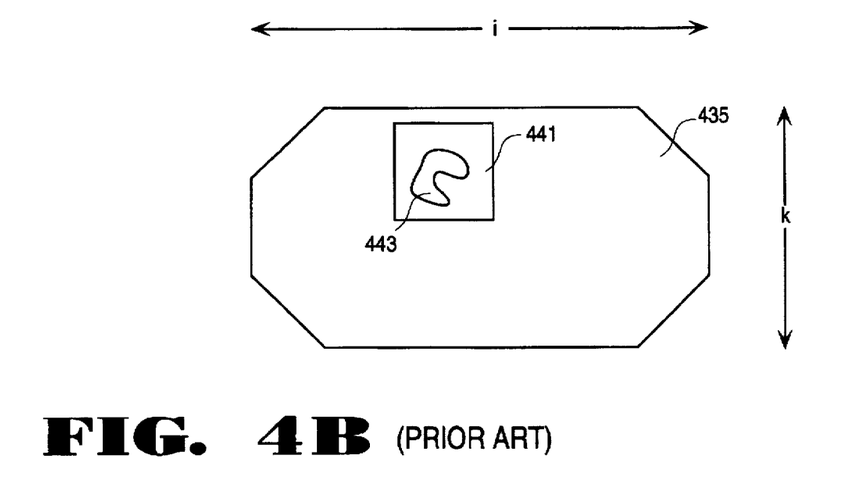

FIGS. 4A and 4B illustrate movement of the roving zoom window during emission scanning. FIG. 4A illustrates the roving zoom window 441 located at an initial position (i, k) within the field of view 435 of a detector 10. An image of the heart 443 is displayed. FIG. 4B illustrates the same configuration at a different rotation angle. The roving zoom region 441 has displaced by some di and dk value. As shown, the roving zoom region 441 has been displaced upward to track the heart so that the image of the heart 443 remains in the field of view of the zoom region for each ECT rotation angle. At the completion of the scan, there is a different offset value (di and dk) for each roving zoom region for each angle of rotation (theta). For example, there is a di(theta) and dk(theta) for the roving zoom region for detector 10 and for detector 12. These offset values are stored in memory. For example, the following dataset can be generated and stored in memory:

| Rotation Angle | Detector 10 | Detector 12 |
|---|---|---|
| theta0 | di(theta0), dk(theta0) | di(theta0), dk(theta0) |
| theta1 | di(theta1), dk(theta1) | di(theta1), dk(theta1) |
| theta2 | di(theta2), dk(theta2) | di(theta2), dk(theta2) |
| theta3 | di(theta3), dk(theta3) | di(theta3), dk(theta3) |
| theta4 | di(theta4), dk(theta4) | di(theta4), dk(theta4) |
| ... | ... | ... |
| thetan | di(thetan), dk(thetan) | di(thetan), dk(thetan) |

Figure 4C:
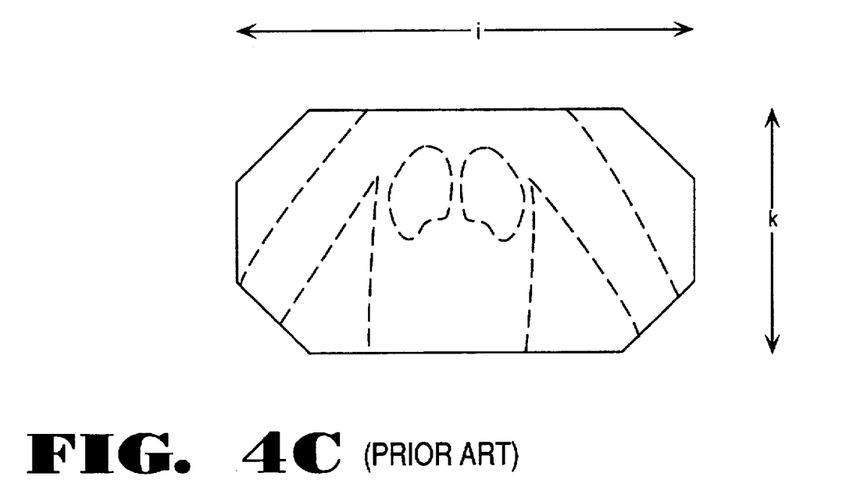
FIGS. 4C and 4D illustrate the adjustment of transmission data according to a spatial offset of a roving zoom region used for emission scanning.
Figure 4D:
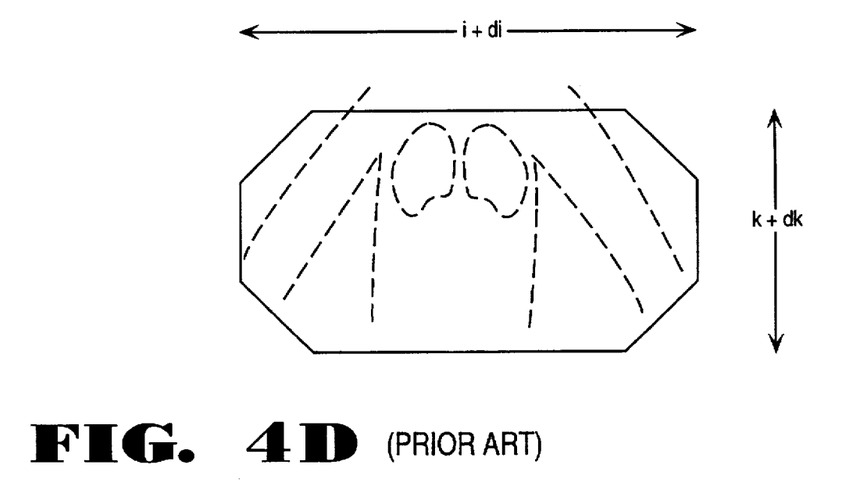

For each rotation angle (theta), the transmission dataset matrix is offset spatially according to the amount of displacement of the roving zoom region for that angle (e.g., by di(theta), dk(theta)). FIGS. 4C and 4D show this effect for a given angle of rotation. Specifically, FIG. 4C illustrates the dataset matrix for a transmission scan of detector 10 without compensation. FIG. 4D illustrates that the transmission data for a given angle theta is offset by di and dk to account for the roving zoom window displacement. By performing this compensation for each dataset of each detector for each angle (theta), the transmission data is effectively translated so that it becomes based on the virtual center of rotation (e.g., the organ) and not the gantry center of rotation. After the spatial compensation is complete, the transmission data matrices are stored in memory.

As mentioned above, because the transmission pixels are larger than the emission pixels, the imaging system adjusts the pixel size of the transmission dataset matrices to match the zoom region pixel size. For instance, assuming the zoom region pixels are at some magnification M larger than 1.0 (e.g., 1.5 magnification), then the pixels of the transmission scan are reduced in size and increased in number and interpolated using a linear interpolation procedure until the pixel sizes from the transmission and the emission scans match. For example, assume the transmission dataset matrices are acquired in matrix sizes of 64×64. The present invention transforms this matrix onto a larger matrix dataset (e.g., 128×128) which effectively reduces the size of the individual pixels of the transmission dataset matrices but increases their number. However, since the magnification M of the emission data can be less than twice magnification, the new transmission matrix may not be completely filled.

Figure 5:
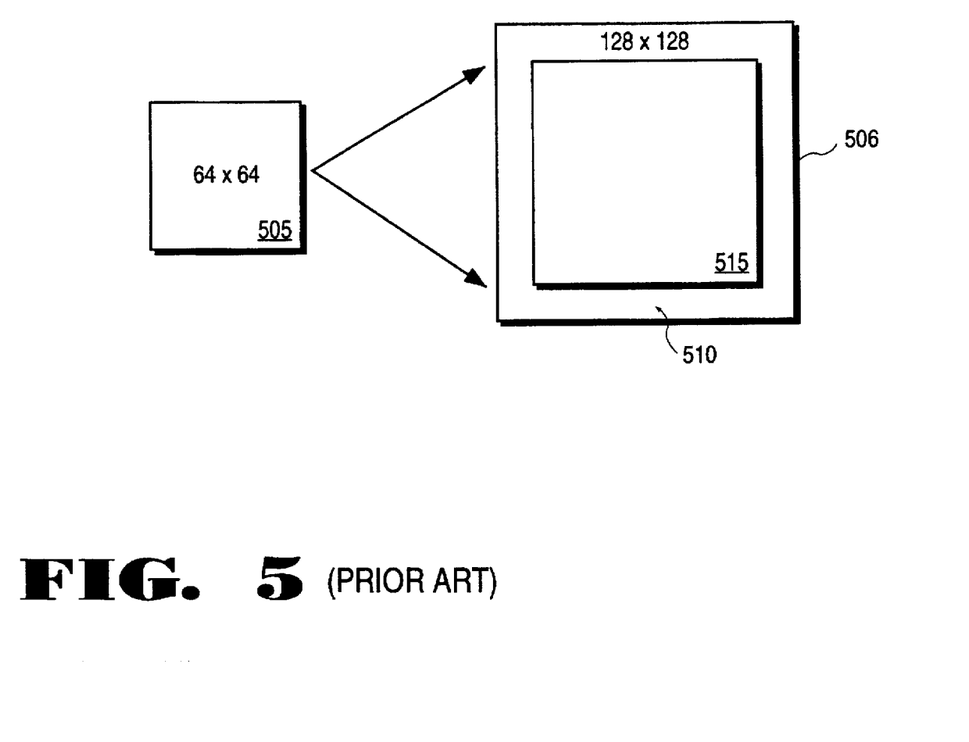
FIG. 5 illustrates a transformation to adjust the pixel size of transmission dataset matrices to match the pixel size of emission dataset matrices.

Referring now to FIG. 5, an exemplary transmission dataset matrix 505 composed of a matrix of 64×64 pixels is shown. The image data of the matrix 505 is transformed into a larger matrix 506 (composed of a matrix of 128×128, for example). The transmission image data from matrix 505 is recorded into "area" 515. The border "area" 510 is empty for situations in which the zoom magnification M is less than two. If, for example, the zoom magnification was 1.5, then each pixel within matrix 505 would be linearly interpolated with its neighboring pixels, such that two adjacent pixels would create additional pixels in between, and so on, until the region 515 was complete and the transmission data was adjusted to the 1.5 zoom magnification. However, since matrix 506 is twice as large in both dimensions as matrix 505 and since M=1.5, the border 510 of the matrix 506 remains empty of valid data.

A number of techniques are available for transforming one image from a first matrix to a second matrix that contains more pixels of a smaller size, individually, as compared to the first matrix. Any of a number of well-known methods may be used within the scope of the present invention.

As noted above, once the transmission dataset has been corrected for the zoom region displacements and pixel size, the transmission image data will be effectively coregistered with the emission image data, since the two datasets were acquired simultaneously using the same imaging system (i.e., using the same detectors).

Figure 6:
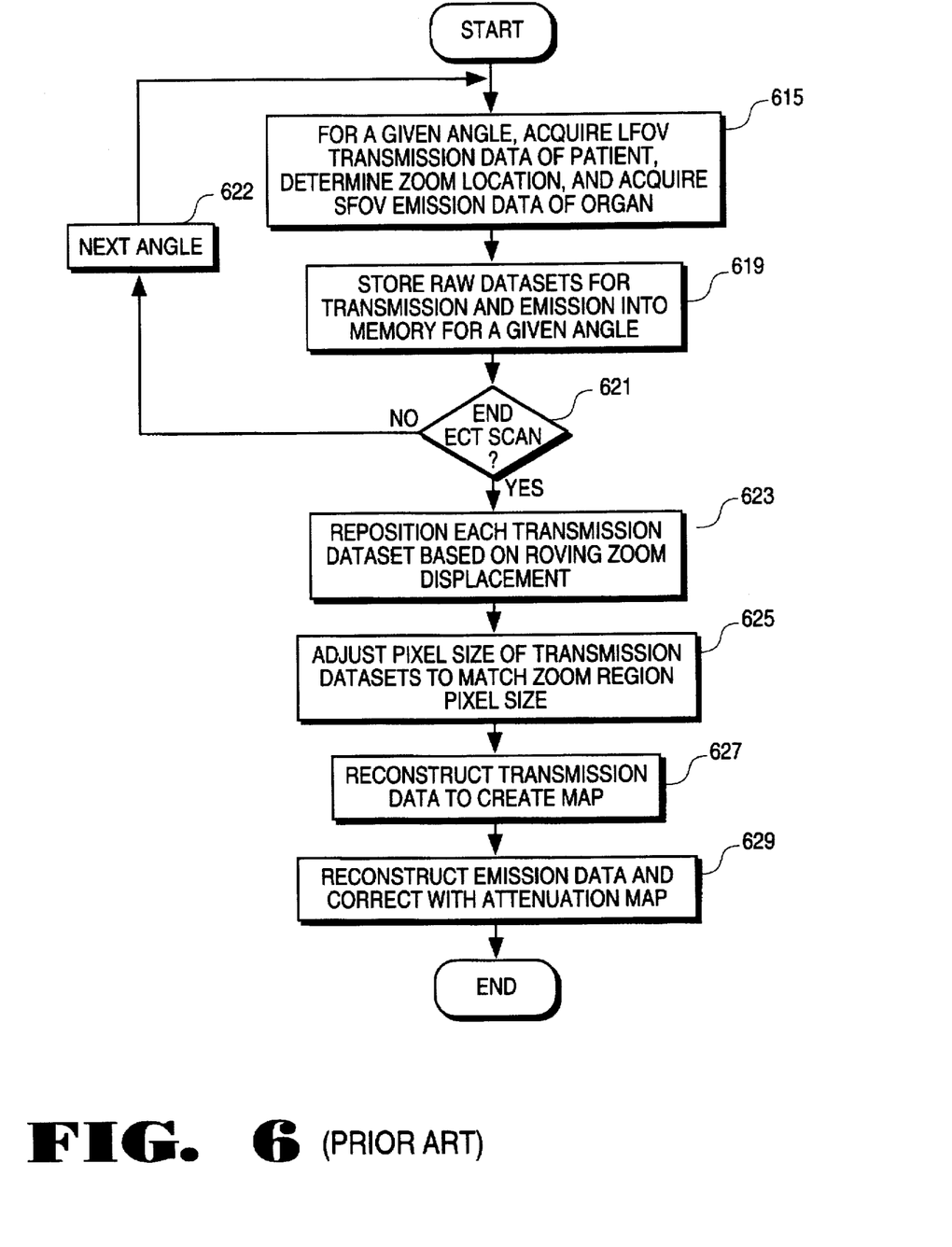
FIG. 6 is a flow diagram illustrating an overall process of data acquisition and image generation using a nuclear medicine imaging system.

FIG. 6 is a flow diagram illustrating an overall process of data acquisition and image generation using a nuclear medicine imaging system. To perform LFOV transmission with SFOV emission, the gantry is first positioned at an initial rotation angle. Detectors 10 and 12 are oriented at 90 degrees to each other. At the initial rotation angle the proper initial positions and sizes of the roving zoom windows (e.g., with respect to the scintillation detectors) are determined as described in U.S. Pat. No. 5,304,806. At block 615, a transmission scan is performed for this rotation angle using the line sources 20 and 22, and imaging information (e.g., transmission data) is recorded across the full FOV of the detectors 10 and 12. Also at block 615, emission data is obtained from the detectors 10 and 12 only from the roving zoom window regions of each detector. It should be appreciated that the transmission data acquisition and the emission data acquisition of block 615 occur simultaneously.

After a predetermined imaging time during which sufficient transmission and emission counts are obtained, at block 619 the imaging system stores the emission image counts as a dataset matrix into a memory device and references this information by the current rotation angle. Also at block 619, the imaging system stores the transmission image counts as a dataset matrix into a memory device and references this information by the current rotation angle. At block 621, the imaging system then determines if the imaging session is complete. If not, then a new angle of rotation is determined, and the detectors 10 and 12 are properly rotated to the new rotation angle at block 622. Processing then returns to block 615 so that the image dataset matrices for the transmission scan and for the emission scan can be completed and stored for this new rotation angle.

At block 621, if the scanning for the last rotation angle is complete, then processing continues to block 623 where the transmission dataset matrices for each detector and for each rotation angle are spatially corrected to account for the virtual center of rotation defined by the roving zoom region. Therefore, for each angle (theta) the transmission dataset matrix is offset spatially according to the amount of displacement of the roving zoom region for that angle theta (e.g., by di(theta), dk(theta)). An illustration of this effect is shown in FIGS. 4C and 4D for a given angle of rotation, as discussed above. After the repositioning of block 621 is complete, the transmission data matrices are stored in memory.

At block 625, the pixel size of the transmission dataset is adjusted based on the magnification factor of the emission dataset. Step 625 is performed for each transmission dataset matrix for each detector for each angle of rotation. The results are stored in memory.

At block 627, the imaging system performs a reconstruction of the transmission information. This reconstruction may be performed for the purpose of generating a nonuniform attenuation map or for other purposes, such as coregistration of multi-modality data according to the present invention. The processes and procedures for reconstructing image information taken at different rotation angles are well known. Any of a number of different and well known reconstruction procedures can be used within the scope of the present invention.

At block 629, the imaging system performs reconstruction of the emission data collected via the roving zoom region. During the reconstruction, the transmission reconstruction map is applied using well known procedures to correct for nonuniform attenuation of the body. Since the transmission reconstruction was corrected for roving zoom displacement (e.g., step 623) and pixel size (e.g., step 625), the transmission reconstruction can be directly applied to the emission reconstruction as a nonuniform attenuation map. The emission reconstruction and attenuation correction can be performed in a number of different ways. In one embodiment of the present invention, it is performed on a "slice-by-slice" basis.

After completion of the above process 610, slices of the emission reconstruction image can be displayed on a CRT or generated in hardcopy using a printer or other equivalent device. Selected slices may be displayed and/or printed out in response to user inputs.

IV. Coregistration of Emission Images with Images of Other Modalities

A given imaging modality (SPECT, PET, MRI, x-ray CT, etc.) may be useful for obtaining a specific type of diagnostic information but not other types of diagnostic information, as noted above. SPECT is often used to obtain images of an organ which show both structural (anatomical) and functional information about that organ. However, SPECT yields little or no information about the anatomical structures surrounding the organ of interest. In contrast, x-ray CT and MRI generally provide images of anatomical structures, such as the lungs and skeletal structures, with relative clarity. Therefore, it is often desirable to coregister nuclear medicine emission (SPECT) images with images from another modality. For example, a physician may wish to view an emission image of the heart as coregistered with an x-ray CT or MRI image of the lungs.

It must be noted that nuclear medicine transmission images obtained using the technique described above also tend to show certain anatomical structures which the emission images do not show, such as the lungs. However, nuclear medicine transmission images often do not provide high resolution. Therefore, while such anatomical structures can be identified in the transmission images, the structures generally do not appear with sufficient clarity or detail to be useful in diagnosis. It must also be noted that the nuclear medicine transmission data, if acquired simultaneously with the emission data using the same detector as the emission data and if processed as described above, is inherently coregistered with the emission data. Therefore, according to the present invention, nuclear medicine transmission images which are coregistered with nuclear medicine emission images are used to coregister the nuclear medicine emission images with images from other modalities (e.g., MRI, x-ray CT, etc.).

Figure 7A:
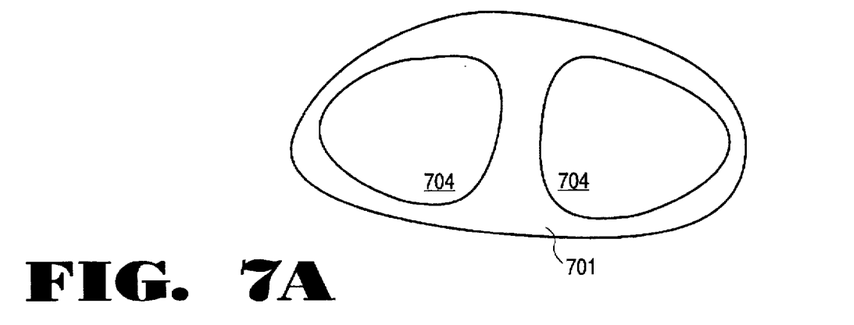
FIG. 7A illustrates a nuclear medicine transmission image.
Figure 7B:
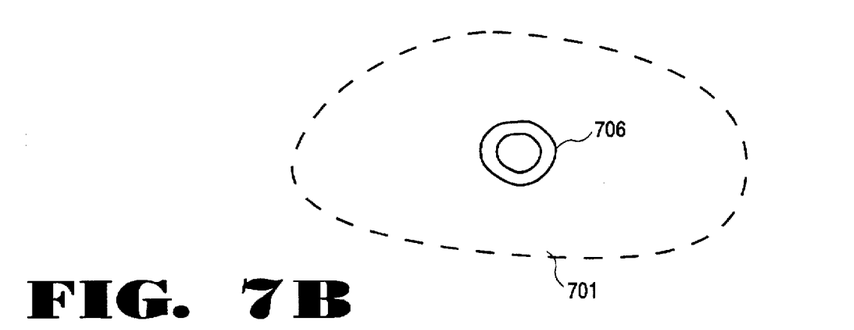
FIG. 7B illustrates a nuclear medicine emission image.

Reference is now made to FIGS. 7A through 7D, which show representations of transaxial "slice" images taken of the chest area of a patient; that is, the images represented by FIGS. 7A through 7D are in a plane that is perpendicular to the long axis of the patient's body. FIG. 7A represents a nuclear medicine transmission image. The transmission image shows the lungs 704 and the outer contour 701 of the patient's body. FIG. 7B represents a nuclear medicine emission image of the same region of the body as FIG. 7A. The emission image of FIG. 7B shows the heart 706 in detail, but shows no other anatomical structure with any useful degree of resolution. The outer contour 701 of the body is also provided in FIG. 7B for reference only, although the contour 701 does not actually appear in the emission image. Although the transmission and emission images are illustrated here separately, assume that the dataset for the emission image of FIG. 7B is coregistered with the dataset for the transmission image of FIG. 7A, as a result of simultaneous data acquisition and processing as described above.

Figure 7C:
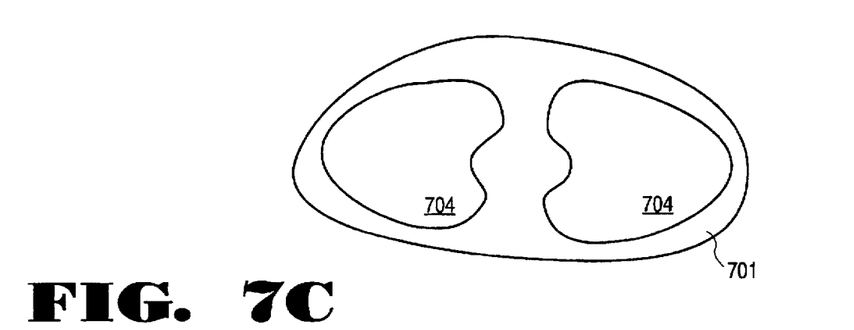
FIG. 7C illustrates an x-ray computed tomography (CT) image.
Figure 7D:
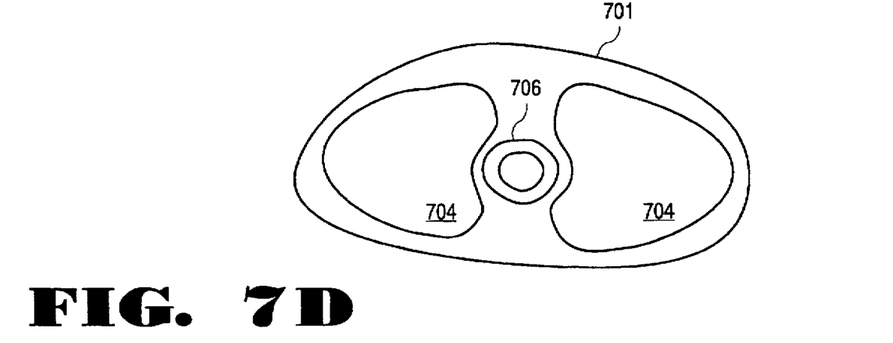
FIG. 7D illustrates the nuclear medicine emission image of FIG. 7B coregistered with the x-ray computed tomography image of FIG. 7C.

FIG. 7C illustrates an x-ray CT image of the same region of the body as FIGS. 7A and 7B. The x-ray CT image of FIG. 7C shows the outer contour 701 of the patient's body. In addition, the x-ray CT image shows the lungs 704 with greater resolution than provided by the transmission image of FIG. 7A. However, because the transmission image of FIG. 7A and the x-ray CT image of FIG. 7C both show the lungs 704, these two images can be coregistered. Once the nuclear medicine transmission image and the x-ray CT image are coregistered, the x-ray CT image is effectively coregistered with the nuclear medicine emission image of FIG. 7B. This is so because the transmission image is already coregistered with the emission image. FIG. 7D illustrates the nuclear medicine emission image of FIG. 7B coregistered with the x-ray computed tomography image of FIG. 7C. The resulting coregistered image shows both the heart 706 and the lungs 704 with useful clarity, thus providing a more informative image for diagnostic purposes than any of the images viewed individually.

Figure 8:
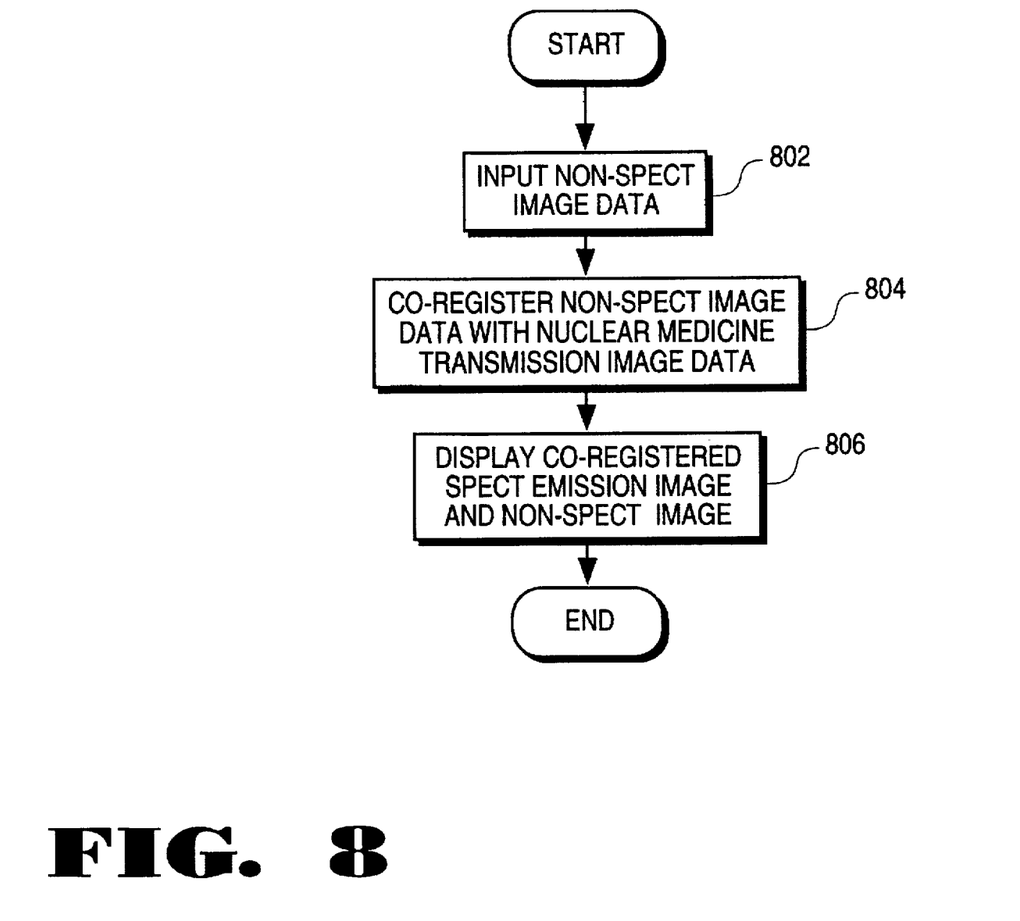
FIG. 8 is a flow diagram illustrating the steps for coregistering data from different modalities.

The overall process of coregistering SPECT images with non-SPECT images is shown in FIG. 8. At block 802, non-SPECT image data is input into a computer system. At block 804, the non-SPECT images are coregistered with the nuclear medicine transmission images. At block 806, the SPECT emission images (the dataset of which is already coregistered with the dataset of the transmission images) are displayed with the non-SPECT images in coregistered form.

The process of coregistering the x-ray CT or other non-SPECT images with the transmission images (in order to coregister the non-SPECT images with the emission images) may be performed either manually or automatically. Manual coregistration may be performed with the aid of a computer system having software that facilitates manipulation of images by a user through a graphical user interface. Various types of software are well-known and widely available for performing such functions. The computer system may be (but is not required to be) part of the imaging system used to acquire the images.

As an example of how images can be manually coregistered using a computer, assume that a transmission image and an x-ray CT image of the same region of the body are displayed on a CRT of the computer system. A user can manipulate a mouse or other cursor control device to align the transmission and x-ray CT images, using common anatomical structures (e.g., the lungs) as visual cues. Once these images are aligned, the emission image can be substituted for the transmission image on the display. Specifically, the emission image can be displayed as lined up to a common reference point on the display as the transmission image. Hence, the x-ray CT image can be superimposed on the emission image, or vice versa, such that the resulting image is the emission image coregistered with the x-ray CT image.

Alternatively, the computer system may be configured with software which will automatically coregister the transmission images with the non-SPECT images. Software for locating and aligning objects within images is available and well known in the art. Such software may use, for example, an edge detection algorithm to locate and align objects in different images.

It should be appreciated that the particular method used to coregister the nuclear medicine transmission images with the non-SPECT images is unimportant; what is important is that such a method can be used as a means of coregistering SPECT (emission) image data with non-SPECT image data.

It should also be appreciated that the x-ray CT image of FIG. 7C is only illustrative. Images from other non-SPECT modalities, particularly MRI, may also be coregistered with SPECT images in the manner described above. Further, it should be noted that the above coregistration technique is not limited in application to the coregistration of transaxial slice images. The technique may be applied to any types of views obtained using medical imaging techniques (e.g., coronal views, etc.).

Thus, a method and apparatus for coregistering medical images of different modalities have been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A method of coregistering medical image data of different modalities, the method comprising the steps of:

performing an emission scan of an object using a nuclear medicine imaging system to acquire single-photon emission computed tomography (SPECT) image data;

performing a transmission scan of the object using the nuclear medicine imaging system to acquire nuclear medicine transmission image data that is coregistered with the SPECT image data;

providing image data of a third modality, wherein the third modality is a modality other than SPECT or nuclear medicine transmission imaging; and coregistering the nuclear medicine transmission image data with the image data of the third modality, such that the image data of the third modality becomes coregistered with the SPECT image data.

2. A method according to claim 1, wherein the step of performing the transmission scan is performed simultaneously with the step of performing the emission scan.

3. A method according to claim 2, wherein a plurality of position values correspond to the nuclear medicine transmission image data, and wherein the step of coregistering the nuclear medicine transmission image data and the SPECT image data comprises the steps of:

determining a plurality of offset values representing spatial offsets between elements of the SPECT image data and corresponding elements of the nuclear medicine transmission image data; and adjusting the position values associated with the nuclear medicine transmission image data based on the offset values.

4. A method according to claim 1, wherein the method is implemented in a computer system.

5. A method according to claim 4, wherein the computer system comprises a display device and an input device, and wherein the step of coregistering comprises the steps of:

displaying a first image on the display device based on the nuclear medicine transmission image data;

displaying a second image on the display device based on the image data of the third modality; and accepting a set of user inputs from the input device, the user inputs for manually repositioning the second image relative to the first image; and outputting a third image based on the SPECT image data positioned according to the set of user inputs.

6. A method according to claim 4, wherein the computer system comprises a processor, and wherein the method further comprises the step of configuring the processor to coregister the set of nuclear medicine transmission image data with the image data Of the third modality, to coregister the SPECT image data with the image data of the third modality.

7. A method according to claim 6, wherein the step of coregistering comprises the step of using the processor to automatically coregister the SPECT image data and the image data of the third modality.

8. In a nuclear medicine imaging system having a detector for receiving radiation and outputting image information, a radiation source for transmitting radiation through an object to a scintillation detector, and a computer system; a computer-implemented method of coregistering medical image data of a plurality of modalities, the method comprising the steps of:

controlling the scintillation detector and the radiation source to simultaneously perform an emission scan of the object to acquire a set of single-photon emission computed tomography (SPECT) image data and a transmission scan of the object to acquire a set of nuclear medicine transmission image data;

coregistering the SPECT data and the nuclear medicine transmission image data;

inputting into the computer system a third set of image data, wherein the third set of image data is of a modality other than SPECT or nuclear medicine transmission imaging; and coregistering the set of nuclear medicine transmission image data with the third set of image data to cause the third set of image data to be coregistered with the SPECT image data.

9. A method according to claim 8, wherein the nuclear medicine transmission image data includes a plurality of position values, and wherein the step of coregistering the nuclear medicine transmission image data and the SPECT image data comprises the steps of:

determining a plurality of offset values representing spatial offsets between elements of the SPECT image data and corresponding elements of the nuclear medicine transmission image data; and adjusting the position values based on the offset values.

10. A method according to claim 8, wherein the computer system comprises a display device and an input device, and wherein the step of coregistering the set of nuclear medicine transmission image data with the third set of image data comprises the steps of:

displaying a first image on the display device based on the nuclear medicine transmission image data;

displaying a second image on the display device based on the third set of image data; and accepting a set of user inputs from the input device, the user inputs specifying a change in the relative positioning of the first image and the second image as displayed on the display device; and displaying a third image on the display device based on the SPECT image data, such that the third image is displayed in a position determined according to the set of user inputs.

11. A method according to claim 8, wherein the computer system includes a processor, and wherein the method further comprises the step of configuring the processor to automatically coregister the set of nuclear medicine transmission image data with the third set of image data in response to a user input.

12. A method according to claim 8, wherein the step of coregistering comprises the step of using the processor to automatically coregister the SPECT image data and the third set of image data.

13. An apparatus for coregistering medical image data of different modalities, comprising:

means for performing an emission scan of an object using a nuclear medicine imaging system to acquire single-photon emission computed tomography (SPECT) image data;

means for performing a transmission scan of the object using the nuclear medicine imaging system to acquire nuclear medicine transmission image data that is coregistered with the SPECT image data;

means for providing image data of a third modality other than SPECT or nuclear medicine transmission imaging; and means for coregistering the nuclear medicine transmission image data with the image data of the third modality, such that the image data of the third modality becomes coregistered with the SPECT image data.

14. An apparatus according to claim 13, wherein the means for performing the transmission scan comprises means for performing the transmission scan simultaneously with the emission scan.

15. An apparatus according to claim 14, wherein the nuclear medicine transmission image data is associated with a plurality of position values, and wherein the means for coregistering the nuclear medicine transmission image data and the SPECT image data comprises:

means for determining a plurality of offset values representing spatial offsets between elements of the SPECT image data and corresponding elements of the nuclear medicine transmission image data; and means for adjusting the position values associated with the based on the offset values.

16. An apparatus according to claim 13, wherein the apparatus further comprises a computer system.

17. An apparatus according to claim 16, wherein the computer system comprises a display device and an input device, and wherein the means for coregistering comprises:

means for displaying a first image on the display device based on the nuclear medicine transmission image data;

means for displaying a second image on the display device based on the image data of the third modality; and means for accepting a set of user inputs from the input device, the user inputs for manually repositioning the second image relative to the first image; and means for outputting a third image based on the SPECT data in a position determined according to the set of user inputs.

18. An apparatus according to claim 16, wherein the computer system comprises means for automatically coregistering the set of nuclear medicine transmission image data with the image data of the third modality.

19. A nuclear medicine imaging system, comprising:

a detector for receiving radiation and outputting image information;

a radiation source for transmitting radiation through an object to the detector; and a computer system coupled to the detector and the radiation source, the computer system including a processor configured to:

control the detector and the radiation source to simultaneously perform an emission scan of the object to acquire a set of single-photon emission computed tomography (SPECT) data and a transmission scan of the object to acquire a set of nuclear medicine transmission data;

coregister the SPECT data and the nuclear medicine transmission data;

input into the computer system a third set of image data of a modality other than SPECT or nuclear medicine transmission imaging; and coregister the set of nuclear medicine transmission data with the third set of image data to cause the third set of image data to be coregistered with the SPECT data.

20. An imaging system according to claim 19, wherein the nuclear medicine transmission data includes a plurality of position values, and wherein the processor is configured to coregister the nuclear medicine transmission data and the SPECT data by:

determining a plurality of offset values representing spatial offsets between elements of the SPECT data and corresponding elements of the nuclear medicine transmission data; and adjusting the position values based on the offset values.

21. An imaging system according to claim 20, wherein the computer system further comprises a display device and an input device, and wherein the processor is configured to coregister the set of nuclear medicine transmission data with the third set of image data by:

displaying a first image on the display device based on the nuclear medicine transmission data;

displaying a second image on the display device based on the third set of image data; and accepting a set of user inputs from the input device, the user inputs specifying a change in the relative positioning of the first image and the second image as displayed on the display device; and displaying, based on the user inputs and the SPECT data, a third image on the display device, such that the second image and the third image are displayed superimposed.

22. An imaging system according to claim 20, wherein the processor is further configured to automatically coregister the set of nuclear medicine transmission data with the third set of image data in response to a user input.

* * * * *